(12) United States Patent
Meek et al.

(10) Patent No.: US 10,383,564 B2
(45) Date of Patent: Aug. 20, 2019

(54) INDICATOR PANELS FOR INCONTINENCE PRODUCTS

(71) Applicant: Pixie Scientific, LLC, New York, NY (US)

(72) Inventors: Scott Meek, New York, NY (US); Yaroslav Faybishenko, New York, NY (US)

(73) Assignee: Pixie Scientific, LLC, New York, NY (US)

( * ) Notice: Subject to any disclaimer, the term of this patent is extended or adjusted under 35 U.S.C. 154(b) by 571 days.

(21) Appl. No.: 15/162,192

(22) Filed: May 23, 2016

(65) Prior Publication Data

US 2016/0338883 A1  Nov. 24, 2016

Related U.S. Application Data

(60) Provisional application No. 62/165,696, filed on May 22, 2015.

(51) Int. Cl.
*A61F 13/42* (2006.01)
*A61B 5/20* (2006.01)
(Continued)

(52) U.S. Cl.
CPC .......... *A61B 5/207* (2013.01); *A61B 5/14507* (2013.01); *A61B 5/6808* (2013.01); *A61B 10/007* (2013.01); *A61F 13/42* (2013.01); *A61B 5/14539* (2013.01); *A61B 2010/0006* (2013.01); *A61F 2013/422* (2013.01);
(Continued)

(58) Field of Classification Search
CPC ................. A61F 13/42; A61F 2013/422; A61F 2013/427; A61F 2013/8473; A61F 2013/8488; A61F 2013/8491; A61B 5/14507; A61B 5/14539; A61B 5/150358; A61B 5/207; A61B 5/6808; A61B 10/007; A61B 2010/0006
See application file for complete search history.

(56) References Cited

U.S. PATENT DOCUMENTS 3,146,070 A   8/1964 Collins et al.
4,318,709 A   3/1982 Falb et al.
(Continued)

FOREIGN PATENT DOCUMENTS

AT    501855 A1    11/2006
CN    102713588 A  10/2012
(Continued)

OTHER PUBLICATIONS

Sep. 29, 2016 Extended European Search Report from the European Patent Office, in EP Application No. 13848690.7, which is a foreign application of Applicant Pixie Scientific, LLC.
(Continued)

*Primary Examiner* — Catharine L Anderson
(74) *Attorney, Agent, or Firm* — Kolitch Romano LLP

(57) ABSTRACT

Indicating panels adapted to provide a qualitative or quantitative indication of a characteristic of a liquid absorbed by the indicator panel. The indicating panels include a porous inner sheet that is impregnated with a first indicator selected to respond to a target analyte by creating a detectable response, and a porous outer sheet impregnated with a polymeric mordant selected to stabilize indicators.

30 Claims, 2 Drawing Sheets

(51) Int. Cl.
  *A61B 10/00* (2006.01)
  *A61B 5/145* (2006.01)
  *A61B 5/00* (2006.01)
  A61F 13/53 (2006.01)
  A61F 13/84 (2006.01)

(52) U.S. Cl.
  CPC .................. *A61F 2013/427* (2013.01); *A61F 2013/530481* (2013.01); *A61F 2013/8473* (2013.01)

(56) References Cited

U.S. PATENT DOCUMENTS

| 5,181,905 | A | * | 1/1993 | Flam .................. A61L 15/56 374/161 |
| 5,516,700 | A | | 5/1996 | Smith et al. |
| 5,922,283 | A | | 7/1999 | Hsu |
| 5,959,535 | A | | 9/1999 | Remsburg |
| 6,060,256 | A | | 5/2000 | Everhart et al. |
| 6,149,865 | A | | 11/2000 | Hsu |
| 6,163,262 | A | | 12/2000 | Wu |
| 6,186,991 | B1 | | 2/2001 | Roe et al. |
| 6,203,496 | B1 | | 3/2001 | Gael et al. |
| 6,436,055 | B1 | | 8/2002 | Roe |
| 6,479,727 | B1 | | 11/2002 | Roe |
| 6,515,194 | B2 | * | 2/2003 | Neading ................. A61F 13/42 604/361 |
| 6,862,466 | B2 | | 3/2005 | Ackerman |
| 6,981,951 | B1 | | 1/2006 | Rahe |
| 7,176,344 | B2 | | 2/2007 | Gustafson et al. |
| 7,187,790 | B2 | | 3/2007 | Sabol et al. |
| 7,314,752 | B2 | | 1/2008 | Kritzman et al. |
| 7,365,238 | B2 | | 4/2008 | Diehl et al. |
| 7,541,177 | B2 | | 6/2009 | Kritzman et al. |
| 7,619,033 | B2 | | 11/2009 | Calhoun et al. |
| 7,846,383 | B2 | * | 12/2010 | Song ..................... A61F 13/42 422/420 |
| 7,947,467 | B2 | | 5/2011 | Kritzman et al. |
| 8,044,257 | B2 | | 10/2011 | Song |
| 8,196,809 | B2 | | 6/2012 | Thorstensson |
| 8,217,217 | B2 | | 7/2012 | Diehl et al. |
| 8,244,638 | B2 | | 8/2012 | Agarwal et al. |
| 8,273,939 | B2 | | 9/2012 | Klofta et al. |
| 8,278,497 | B2 | | 10/2012 | Klofta et al. |
| 8,293,967 | B2 | | 10/2012 | Klofta et al. |
| 8,506,901 | B2 | | 8/2013 | Chen et al. |
| 9,131,893 | B2 | | 9/2015 | Faybishenko et al. |
| 9,486,368 | B2 | * | 11/2016 | Nelson ............. A61F 13/15699 |
| 2002/0145526 | A1 | | 10/2002 | Friedman et al. |
| 2003/0158530 | A1 | | 8/2003 | Diehl et al. |
| 2004/0078219 | A1 | | 4/2004 | Kaylor et al. |
| 2004/0113801 | A1 | | 6/2004 | Gustafson et al. |
| 2004/0118704 | A1 | | 6/2004 | Wang et al. |
| 2004/0220538 | A1 | | 11/2004 | Panopoulos |
| 2005/0101841 | A9 | | 5/2005 | Kaylor et al. |
| 2008/0025154 | A1 | | 1/2008 | MacDonald |
| 2008/0266117 | A1 | | 10/2008 | Song et al. |
| 2008/0306461 | A1 | | 12/2008 | Jan |
| 2009/0155122 | A1 | | 6/2009 | Song |
| 2009/0157024 | A1 | | 6/2009 | Song |
| 2012/0063652 | A1 | | 3/2012 | Chen et al. |
| 2012/0106811 | A1 | | 5/2012 | Chen et al. |
| 2012/0173249 | A1 | | 7/2012 | Popp et al. |
| 2012/0201437 | A1 | | 8/2012 | Ohnemus |
| 2013/0126347 | A1 | | 5/2013 | Krassnitzer et al. |
| 2013/0136347 | A1 | | 5/2013 | Wachtell et al. |
| 2013/0211731 | A1 | | 8/2013 | Woltman |
| 2013/0273666 | A1 | | 10/2013 | Chen et al. |
| 2014/0121487 | A1 | | 5/2014 | Faybishenko et al. |
| 2014/0294265 | A1 | | 10/2014 | Chen et al. |

FOREIGN PATENT DOCUMENTS

| DE | 29709497 U1 | 9/1997 |
| DE | 19837678 A1 | 3/2000 |
| EP | 0911000 A1 | 4/1999 |
| EP | 1477110 A1 | 11/2004 |
| GB | 2388898 A | 11/2003 |
| JP | 2012-105839 A | 6/2012 |
| JP | 2012105839 A | 6/2012 |
| KR | 20140130879 A | 11/2014 |
| WO | 9424557 A1 | 10/1994 |
| WO | 0065348 A2 | 11/2000 |
| WO | 02048983 A1 | 6/2002 |
| WO | 03009224 A1 | 1/2003 |
| WO | 05017683 A2 | 2/2005 |
| WO | 2006047815 A1 | 5/2006 |
| WO | 07069968 A1 | 6/2007 |
| WO | 2007073139 A1 | 6/2007 |
| WO | 2009121043 A2 | 10/2009 |

OTHER PUBLICATIONS

Dec. 7, 2017, International Preliminary Report on Patentability from the U.S. Receiving Office in PCT/US2016/033785, which is the international application to this U.S. application.
Jan. 11, 2018, Office action from the U.S. Patent and Trademark Office, in U.S. Appl. No. 14/817,638, which is another application of Applicant Pixie Scientific, LLC.
State Intellectual Property Office, Third Office Action in Application No. 201380068010.2, dated Apr. 17, 2018, which is a foreign application of Applicant Pixie Scientific, LLC.
May 2, 2014, International Search Report of the International Searching Authority from the U.S. Receiving Office, in PCT Application No. PCT/US2013/067150, which is an international application of Applicant Pixie Scientific, LLC.
May 2, 2014, Written Opinion of the International Searching Authority from the U.S. Receiving Office, in PCT Application No. PCT/US2013/067150, which is an international application of Applicant Pixie Scientific, LLC.
May 9, 2014, Office action from the U.S. Patent and Trademark Office, in U.S. Appl. No. 14/065,360, which is another application of Applicant Pixie Scientific, LLC.
Feb. 11, 2015, final Office action from the U.S. Patent and Trademark Office, in U.S. Appl. No. 14/065,360, which is another application of Applicant Pixie Scientific, LLC.
Apr. 28, 2015, International Preliminary Report on Patentability from the International Bureau of WIPO, in PCT Application No. PCT/US2013/067150, which is an international application of Applicant Pixie Scientific, LLC.
Dec. 1, 2016, First Office Action from the State Intellectual Property Office of China, in Chinese Application No. 2013800680102, which is a foreign application of Applicant Pixie Scientific, LLC.
Jun. 2, 2016 Supplementary Partial European Search Report from the European Patent Office, in EP Application No. 13848690.7, which is a foreign application of Applicant Pixie Scientific, LLC.
Aug. 31, 2016, International Search Report from the U.S. Receiving Office in PCT/US2016/033785, which is the international application to this U.S. application.
Aug. 31, 2016, Written Opinion from the U.S. Receiving Office in PCT/US2016/033785, which is the international application to this U.S. application.
Dec. 11, 2018, Extended European Search Report from the European Patent Office, in European Patent Application No. 16800605.4, which is a foreign application of Applicant Pixie Scientific, LLC.

* cited by examiner

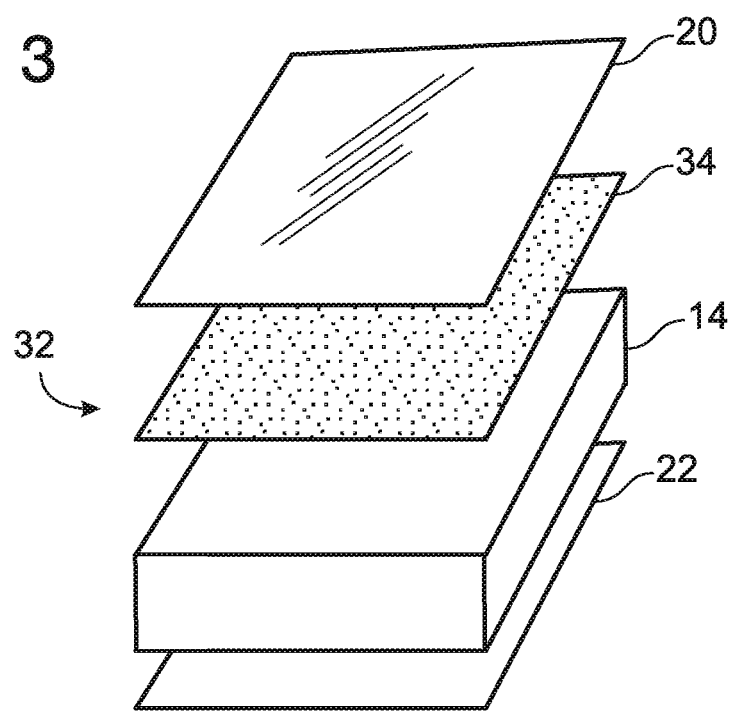

INDICATOR PANELS FOR INCONTINENCE PRODUCTS

CROSS-REFERENCE TO RELATED APPLICATIONS

The present application claims the benefit of priority under 35 U.S.C. § 119(e) of prior provisional application Ser. No. 62/165,696 for INDICATOR PANELS FOR INCONTINENCE PRODUCTS, filed May 22, 2015, which is hereby incorporated by reference.

INTRODUCTION

A variety of ailments and disorders may be detected and/or diagnosed by analysis of a subject's urine sample. For example, the content of a urine sample potentially carries evidence of developing under-hydration or infection, or of endocrine or metabolic system problems. Unfortunately, urine analysis is typically performed in a clinical or laboratory setting, and therefore requires both time and expense.

Existing diagnostic tools for monitoring a specified characteristic of the urine may include colorimetric test strips. Such test strips typically include appropriate detection reagents that are, or are coupled with, colorimetric dyes. However, the colors of such dyes typically shift upon drying, and/or are intrinsically unstable. As a result, the initial color of the test strip may fade after the initial test is completed.

What is needed is a colorimetric indicator system for testing one or more characteristics of a urine sample that is capable of producing an indicative color change that is both distinctive and stable over time.

In particular, the availability of a stable colorimetric indicator system would permit urine testing to move beyond the necessity of collecting a urine sample, with its attendant inconvenience and potential for contamination, improper handling, and/or spilling the sample, and the necessity of immediate reading or interpretation of the colorimetric response.

Embodiments of the colorimetric test systems and methods of the present disclosure may enable the detection of potential health concerns by permitting the testing of a subject's urine through the routine use of an incontinence product that incorporates the colorimetric test system.

SUMMARY

The present disclosure is directed to Indicating panels that may be adapted to provide a qualitative or quantitative indication of a characteristic of a liquid absorbed by the indicator panel.

In one aspect, the present disclosure is directed to an indicating panel for an incontinence product, including a porous inner sheet that is impregnated with a first indicator selected to respond to a target analyte by creating a detectable response, as well as a porous outer sheet adjacent to the inner sheet, the outer sheet being impregnated with a polymeric mordant selected to stabilize indicators that generate detectable responses.

In another aspect, the present disclosure is directed to an indicating incontinence product that includes an absorbent core, a porous inner sheet adjacent to the absorbent core that is impregnated with a first indicator selected to respond to a target analyte by creating a detectable response, and a porous outer sheet adjacent to the inner sheet, where the outer sheet is impregnated with a polymeric mordant selected to stabilize indicators that generate detectable responses.

In yet another aspect, the present disclosure is directed to an indicating panel for an incontinence product that includes a porous inner sheet impregnated with a pair of coupled indicators, the first indicator of the coupled pair being selected to respond to a target analyte by creating a reporting condition, and the second indicator being selected to respond to the reporting condition by generating a detectable response. The indicating panel additionally includes a porous outer sheet adjacent to the inner sheet, the outer sheet being impregnated with a polymeric mordant selected to irreversibly stabilize the second indicator that is generating the detectable response. The indicating panel additionally includes a reference panel disposed adjacent to the absorbent core, where the reference panel includes a substantially white and porous material.

BRIEF DESCRIPTION OF THE DRAWINGS

FIG. 3 is a partially exploded sectional view of an alternative incontinence product of the present disclosure.

DETAILED DESCRIPTION

The present disclosure is directed to indicating systems and methods for incontinence products. The indicating system may include an indicator panel for an incontinence product that is adapted to provide a qualitative or quantitative indication of a characteristic of a liquid absorbed by the indicator panel.

Embodiments of Indicating Systems

Figure 1:
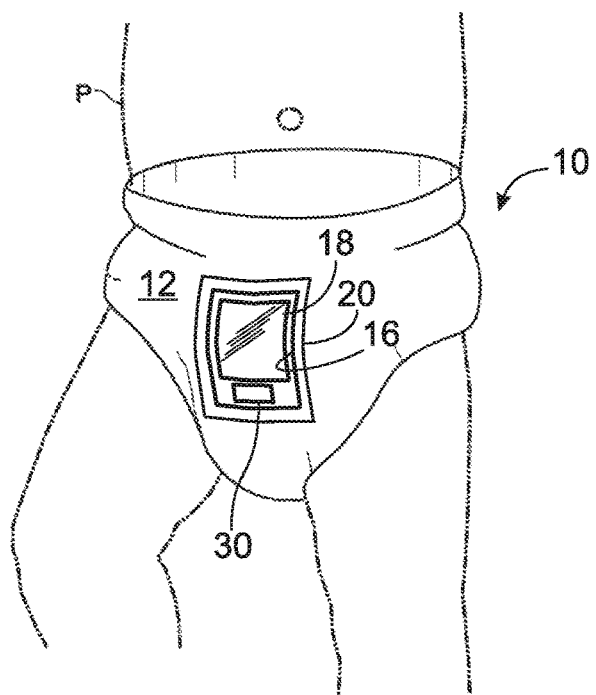
FIG. 1 depicts an embodiment of an incontinence product according to an embodiment of the present disclosure.

FIG. 1 depicts an illustrative incontinence product 10 worn by a patient P according to selected aspects of the present disclosure. Incontinence product 10 is depicted as a diaper, but it should be appreciated that the embodiments of the present disclosure may confer benefits and advantageous properties on any of a variety of incontinence products, including, among others, diapers for a human infant, toddler, child, or adult or a pet animal, or incontinence pads which may be inserted into a patient's underwear. It should be appreciated that the title of patient is intended to include all suitable subjects (e.g., humans, animals, etc.) and is thus not limited to hospital use or use by medical professionals.

Figure 2:
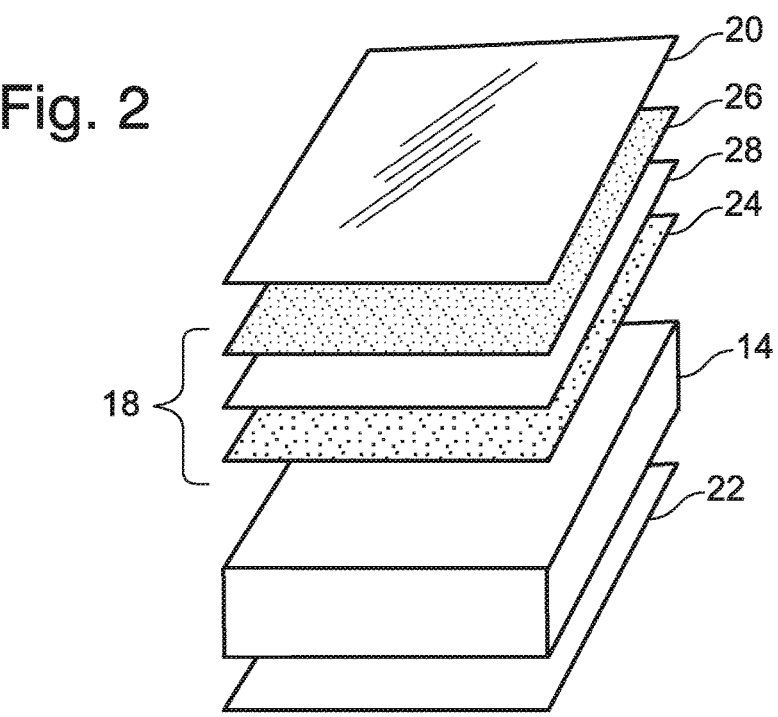
FIG. 2 is a partially exploded sectional view of the incontinence product of FIG. 1.

Diaper 10 of FIG. 1 may be disposable or reusable either partially or totally, and may include an outermost layer 12. The outermost layer may be coupled to an absorbent core 14, as shown in FIG. 2), where the absorbent core 14 may include a superabsorbent polymer, such as sodium polyacrylate polymer, that may be capable of absorbing up to several hundred times its mass in water. Diaper 10 may include a cut-out 16 in the top layer 12 to accommodate an indicator panel 18. Indicator panel 18 may be disposed in cut-out 16 and thereby in contact with absorbent core 14. In one embodiment of the present disclosure, transparent tape 20 may be disposed over indicator panel 18 and a portion of waterproof layer 12 to seal cut-out 16.

Transparent tape 20 may be transparent waterproof film, such as OPSITE® FLEXIFIX® Transparent Film, disposed over indicator panel 18 to provide a sufficient seal and/or to allow indicator panel 18 to be properly viewed, which may allow a user to easily view the indicator panel without removing diaper 10 from its wearer.

Diaper 10 may include any suitable configuration of diaper layers and components for collecting a sample, such as urine, providing for patient comfort, providing for convenience of use and/or viewing the indicator penal 18. An optional privacy cover layer (not shown) may be removably attached and configured to diaper 10 so that diaper 10 has an appearance of a regular diaper, which may be desirable for maintaining confidentiality.

FIG. 2 depicts a partially exploded cross-sectional view of a portion of diaper 10. As shown, diaper 10 may include a permeable innermost layer 22, absorbent core 14, and top layer 12 which may include one or more layers and may be waterproof. Innermost layer 22 may be in contact with a crotch region of the wearer when diaper 10 is being worn. A urine sample produced by the patient may contact innermost layer 22, travel through absorbent core 14, and then contact and/or permeate indicator panel 18.

FIG. 2 additionally depicts an exploded cross-sectional view of indicator panel 18, which may include a porous inner sheet 24 that may be adjacent to and in contact with the absorbent core 14. Inner sheet 24 includes an indicator configured to generate a detectable response when contacting by a liquid including a target analyte.

A target analyte may be the presence or concentration of any component of a patient's sample that may be indicative of, or correlated with, the patient's health or well-being. For example, in one aspect of the present disclosure the detection of a particular marker characteristic in a sample may be indicative of a specific health condition, ailment, or injury. The target analyte may be the presence of one or more substances in the sample that are not generally present, or the target analyte may be a substance in concentration or range of concentrations that correlate with a health condition. For example, the presence of dissolved salts in a urine sample may be normal, but an elevated concentration of those same salts may indicate dehydration or other health issue.

The first indicator may be selected to respond to the target analyte by creating a detectable response. A detectable response, as used herein, is a change in a property of the indicator that is capable of being perceived, either by direct visual observation or instrumentally, preferably by direct visual observation. The detectable response may be colorimetric (color-changing) or luminescent (such as fluorescent), and may be the appearance or disappearance of color, or a shift in absorbance wavelength or, in the case of fluorescence, a shift in emission wavelength. In one aspect of the present disclosure, the detectable response is a color change, and preferably a change from substantially colorless to highly colored.

It may be advantageous to utilize an indicator that may be at least somewhat selective for the target analyte, that is, an indicator that generates comparatively few false positives. The indicator may be selective for a target analyte that is an ion, such as $Cl^-$, $Na^+$, $K^+$, $Ca^{2+}$, $Mg^{2+}$, $Zn^{2+}$, among others. Alternatively, the indicator may be selected for a target analyte that is sample pH.

A number of polydentate chelating moieties (or complexones) may exhibit specificity for complexing particular ions. These chelating moieties may include amine binding groups or carboxylic acid binding groups, and may include without limitation ethylenediamine, EDTA, BAPTA, APTRA, crown ethers, etc. Once a suitable chromophore or fluorophore reporter molecule is bound to such a chelating moiety, the spectral properties of the reporter may detectably change upon the binding of the target ion. A variety of such indicators and their structures may be found in *The Molecular Probes Handbook* 11$^{th}$ *Edition*, 2010, hereby incorporated by reference.

In one aspect of the present disclosure, inner sheet 24 may include a pair of coupled indicators, where the first indicator may be selected to the target analyte by creating a reporting condition that is measurably distinct from the condition the inner sheet prior to exposure to the sample, or measurably distinct from the condition of the first indicator when exposed to a control sample. The second indicator of the coupled pair may be selected to generate a detectable response when the first indicator creates a reporting condition. For example, the reporting condition may be a change in pH, and the second indicator may generate a change in color in response to the change in pH.

Where the indicator panel includes a pair of coupled indicators, the indicators are screened to insure that they are compatible, and that the desired characteristic(s) of the patient sample can be determined. For example, the indicator poly(methyl vinyl ether-alt-maleic acid (PMVEMA) couples effectively with colorimetric indicators that are overall negatively charged, but may be less effective when coupled with neutral or positively charged indicators. Where necessary, one or more of the indicator components of the indicator panel may be titrated to determine whether the useful detection range of that indicator will offer a suitably distinct color change under the expected sample conditions.

Indicator panel 18 may further include a porous outer sheet 26 disposed adjacent to the porous inner sheet 24, or separated from the inner sheet by a separation layer 28. Where a separation layer 28 is present, the separation layer may be selected to be porous, or to be soluble in aqueous solutions, so that the separation layer does not interfere with liquid transport from the inner sheet 24 to the outer sheet 26.

If present, the separation layer may be formed from a suitable dissolvable or porous material, and then placed between the inner and outer sheets of the indicator panel. In some instances, the separation layer may be applied by spray deposition. Suitable porous materials may include, without limitation, polymer fiber sheets, silica gel, or alumina. Suitable dissolvable materials may include, without limitation, polyvinyl alcohol (PVA) or partially hydrolyzed polyvinyl acetate (PVOAc), polyvinylpyrrolidone (PVP), polyethylene glycol (PEG), polyacrylamide, poly(methyacrylic acid), and copolymers or mixtures of any of these. Alternatively, or in addition, the separation layer may be a composite material that include both a water-soluble polymer and a porous and non-dissolving component, including cellulose, polymer fibers, silica, and alumina.

Outer sheet 26 may incorporate a polymeric mordant that is selected to stabilize an indicator that may be exhibiting a detectable response. The polymeric mordant may be selected to immobilize the indicator, or otherwise prevent the detectable response from reverting or fading over time. In this way the examination of outer sheet 26 provides an accurate and stable result that reflects the presence or absence of the target analyte in the sample.

In one aspect of the present disclosure, the polymeric mordant may be a polymer that is derivatized by both hydrophilic and hydrophobic functional groups, such as a polymeric cationic surfactant. In a more specific aspect, the polymeric mordant includes poly[methyl acrylate-co-(3-acrylamidopropyl)trimethyl ammonium chloride]. The polymeric mordant may be selected to be capable of binding or immobilizing the first indicator and second indicator (when present).

Inner sheet 24 and outer sheet 26 are independently selected from any appropriately hydrophilic, absorbent, and/ or porous materials. The composition of the inner and outer sheets may be selected to be substantially chemically and biologically inert with respect to biological fluids and the typical components present therein. In one aspect of the present disclosure, the inner and outer sheet are independently formed from a polymeric fiber, silica gel, or alumina pad. Where one or the other sheet includes polymeric fiber, it may be cellulosic fiber.

In another aspect of the disclosed indicator panel, the polymeric mordant selected to stabilize an indicator may have been stabilized with respect to basic degradation, thermal degradation, and cross-reactivity. For example, where the polymeric mordant is derivatized by quaternary ammonium functional groups, the polymeric mordant may be stabilized by replacing those protons positioned beta to the quaternary ammonium group with lower alkyls having 1-6 carbons (see Scheme 1 below). In this way, the functional group is no longer susceptible to the Hofmann Elimination reaction (see Scheme 2 below), and the polymeric mordant is thereby stabilized with respect to both basic and thermal degradation.

Scheme 1

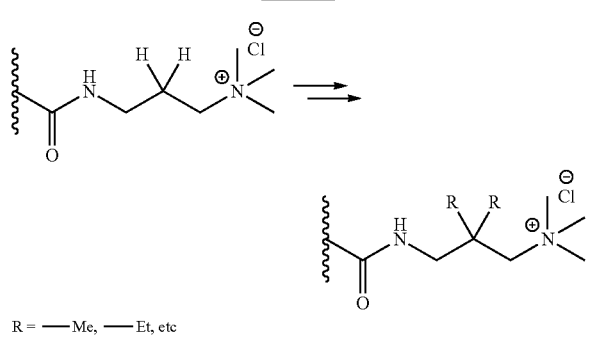

R = —Me, —Et, etc

Scheme 2

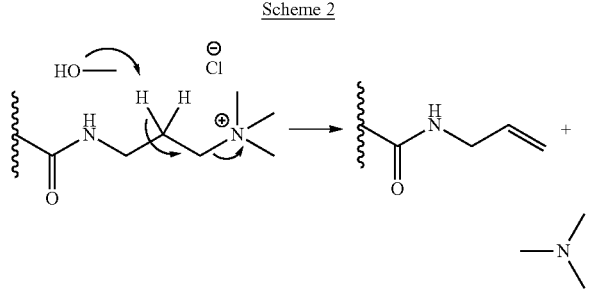

The selection of a stabilized polymeric mordant may permit the manufacture of indicator panels having fewer layers, due to the ability of the stabilized polymeric mordant to stabilize an indicator that may be exhibiting a detectable response. For example, FIG. 3 depicts a partially exploded cross-sectional view of a portion of an alternative diaper, including an indicator panel 32. Unlike indicator panel 18 of FIG. 2, indicator panel 32 includes a single porous inner sheet 34 that may be adjacent to and in contact with the absorbent core 14, and that includes a stabilized polymeric mordant.

As the polymeric mordant of inner sheet 34 may be stable with respect to thermal degradation and basic degradation, the inner sheet 34 may additionally include an indicator configured to generate a detectable response when contacting by a liquid exhibiting a target analyte, or alternatively inner sheet 34 may include a pair of coupled indicators as described above, thereby minimizing the number of layers required for the indicator panel of the present disclosure.

The indicator panels 18 and 32 may be configured, and the coupled indicators selected, so that a desired and suitably distinct color change occurs in the presence of the target analyte. The color change may be selected so that a simple visual inspection will reveal a positive diagnostic response. Alternatively, or in addition, it may be advantageous to inspect the indicator panel using a data acquisition device, such as a camera or optical scanner, that may be coupled directly or indirectly with a processor configured to process and/or analyze the acquired data.

For example, the data acquisition device may include a smartphone camera, and the processor may be the smartphone processor executing an application that may be configured to analyze the acquired diagnostic data. Alternatively, or in addition, the data acquisition device may be directly or indirectly coupled to remote server via an online service (or network). Suitable data acquisition and transmission devices have been described in application Ser. No. 14/065,360 to Faybishenko, hereby incorporated by reference for all purposes.

Under some conditions, a subject's urine may itself be sufficiently highly-colored that the optical contribution of the urine to the apparent color of the indicator panel 18 may adversely affect the ability to accurately perceive or measure the color of the indicator panel. This may be particularly true where the subject's urine may be highly concentrated, and so may have a darker yellow or brown color. Whether the color of the indicator panel may be determined by simple visual observation, or by instrumental means, it may be advantageous for diaper 10 to employ a reference panel 30 (see FIG. 1) as a control for the effect of urine color on the observed color of indicator panel 18 or 34.

Reference panel 30 may be disposed within cut-out 16 in the top layer 12, and may be disposed adjacent to the indicator panel, so that the reference panel 30 may also be in contact with absorbent core 14. The reference panel 30 may be disposed beneath waterproof layer 12 to prevent leaking. Reference panel 30 may include a porous material configured to absorb urine from the absorbent core 14 and to retain and display the color of the urine. The porous material of reference panel 30 may be selected so that it does not alter the color of the subject's urine upon absorption, or over time, and does not itself undergo a shift in color over time in the presence of the subject's urine. Additionally, the material of reference panel 30 (in the absence of urine) should be substantially white in hue, so that an accurate perception and/or measurement of the color of any absorbed urine may be obtained. The reference panel may include a cellulose material, such as for example a cellulose-based filter paper. In one aspect of the disclosed diaper or pad, the reference panel 30 may incorporate filter paper that is WHATMAN filter paper.

Possible Advantages of Embodiments of the Invention

By creating diapers or pads with attached indicating panels, the necessity of dipping urine analysis strips into a cup with urine may be eliminated. In one aspect of the present disclosure, the indicating panel may be configured so that a detectable color change at the outer surface of the outer sheet corresponds to a potentially negative result, so that the appearance of color on the outer surface of the diaper provides an attention-getting signal as to the patient's condition. The detectable color change of the present indicator panels may be additionally stable over time, so that even if the test result is not observed immediately, the test result may remain valid.

The present indicating panels are ideally suited for incorporation into disposal diapers and pads that are used regularly or routinely, as they provide an unobtrusive and non-intrusive means of monitoring one or more patients without the necessity of requiring them to undergo a testing procedure or collecting a specific sample, while the color stability of the present indicating panels permit the test result to be obtained at a time that may be convenient for the care-giver, for example, when the incontinence product would normally be changed.

By using one such diaper, a caregiver may understand over a period of time whether a child or other patient may be becoming dehydrated, for example, or developing any of a variety of other illnesses. This utility may be particularly advantageous in nurseries, child-care facilities, long-term care facilities, and even in the home.

Selected Embodiments of Indicator Panels

The following examples of indicators and indicator systems are intended to set out various operational principles and preferred embodiments, and should be considered to limit the scope of the present disclosure. It will be apparent to those skilled in the art that various changes in form and detail may be made to these examples without departing from the spirit and scope of the disclosure.

Example 1. Indicator Panel for Calcium Ions

An exemplary indicator panel for sensing calcium ions in a patient sample is constructed with an inner sheet that is impregnated with either cresolphthalein-complexone or thymolphthalein-complexone. In addition, the inner sheet includes a somewhat basic buffering agent, such as tris (hydroxymethyl)aminomethane or borate, and a Mg inhibitor to prevent the presence of $Mg^{2+}$ ions from interfering with $Ca^{2+}$ detection. Appropriate Mg inhibitors may include 9-hydroxyquinoline and sulfonated derivatives thereof. The indicator panel may further include an outer sheet that is impregnated with a polymeric mordant that is poly[methyl acrylate-co-(3-acrylamidopropyl)trimethyl ammonium chloride].

The inner sheet may be prepared by impregnating a cellulose sheet with the selected indicator to a concentration of 0.5-1 wt %, with a buffering agent to a concentration of 1-2 wt %, and with the Mg inhibitor to a concentration of 1-2 wt %. The outer sheet may be prepared by impregnating a cellulose sheet with a polymeric mordant such as Poly [methyl acrylate-co-(3-acrylamidopropyl)trimethyl ammonium chloride]. The inner and outer sheets are laminated with an optional separation layer, and disposed on a diaper so that the inner sheet contacts the absorbent core of the diaper.

Where the indicator panel employs a single inner sheet, the inner sheet may be prepared by impregnating a cellulose sheet with the selected indicator to a concentration of 0.5-1 wt %, with a buffering agent to a concentration of 1-2 wt %, a polymeric mordant such as poly[methyl acrylate-co-(3-acrylamidopropyl)trimethyl ammonium chloride] to a concentration of 6-10 wt %, and with the Mg inhibitor to a concentration of 1-2 wt %.

A strong calcium chelator, such as EDTA, may also be added to the calcium sensor in concentrations of 0-5%. Such a sensor may exhibit a muted color response to the presence of calcium ions until the available chelator is bound, at which point free calcium can bind to the indicator dye. The addition of EDTA can sharpen the resolution of the sensor at various calcium levels, and an array of such sensors, each with a different EDTA level, can be used to increase the accuracy of calcium detection.

For an indicator panel that includes cresolphthalein-complexone, when a liquid sample such as urine passes through the absorbent core and into the inner sheet, the buffering agent renders the pH of the liquid somewhat basic. Under basic conditions the cresolphthalein-derived indicator binds $Ca^{2+}$ ions, and then undergoes a detectable color change to a deep red/purple color. The presence of the $Mg^{2+}$ inhibitor 8-hydroxyquinoline prevents interference by $Mg^{2+}$ in the sample. The $Ca^{2+}$ indicator complex then diffuses into the outer sheet and binds strongly with the polymeric mordant. The intense color of the indicator on the outer surface of the indicator panel indicates the presence of, or the presence of a target amount of, $Ca^{2+}$ in the sample.

Example 2. Indicator Panel for Specific Gravity

An adult urine sample may typically have a specific gravity in the range of 1.000 to 1.030, and observation of an increase in urine specific gravity may reflect a number of health issues, including for example dehydration, diarrhea, emesis, UTI, aglucosuria, and renal artery stenosis, among many others. A urine specific gravity greater than 1.035 may be consistent with serious dehydration.

An indicator panel configured to detect high specific gravity may be constructed by impregnating an inner sheet with a first indicator and second indicator. The first indicator may be poly(methyl vinyl ether-alt-maleic acid (PMVEMA), a polymer that responds to increased salt concentrations by lowering local pH. The PMVEMA polymer may be titrated to the desired pH level before use. The second indicator may be a pH indicator that may be bromothymol blue or a related dye, and the inner sheet may be impregnated with the bromothymol blue indicator to a concentration of 1-2 wt %, and impregnated with the titrated PMVEMA to a concentration of 13-15 wt %.

The outer sheet may be prepared by impregnating the sheet with a polymeric mordant that is poly[methyl acrylate-co-(3-acrylamidopropyl)trimethyl ammonium chloride] to a concentration of 9-11 wt %.

While the specific gravity of urine may be due to the presence of proteins or other components other than ion content, measured values of ionic strength can be correlated with specific gravity. When a urine sample passes through the absorbent core and into the inner sheet, the titrated PMVEMA changes the local pH in response to the ionic strength of the urine sample. The pH indicator bromothymol blue then changes color in response to the pH change, and as it diffuses into the outer sheet, the polymeric mordant immobilizes the indicator.

The color of the indicator on the outer surface of the indicator panel indicates that the urine sample exhibits a high specific gravity.

It should be appreciated that the specific components of the disclosed indicator panels may be selected so that the indicator panel, and the incontinence product it may be attached to, may be useful for any of a number of target analytes. For example, indicator panels may be prepared to detect and/or quantify the presence of creatinine, magnesium ions, ketones, and L-dopa, among others.

Example 3. Selected Embodiment

The following numbered paragraphs may describe one or more embodiments according to the present disclosure:

A0. An indicating panel for an incontinence product, comprising:
a porous inner sheet that is impregnated with a first indicator;
    wherein the first indicator is selected to respond to a target analyte by creating a detectable response; and
a porous outer sheet adjacent to the inner sheet, wherein the outer sheet is impregnated with a polymeric mordant selected to stabilize indicators that generate detectable responses.

A1. The indicating panel of paragraph A0, wherein the porous inner sheet further includes a second indicator, wherein the second indicator is selected to respond to the detectable response of the first indicator by generating a second detectable response.

A2. The indicating panel of paragraph A0, further comprising a separation layer disposed between the inner sheet and the outer sheet, wherein the separation layer is at least one of water-soluble and porous.

A3. The indicating panel of paragraph A0, wherein the first indicator is a colorimetric indicator.

A4. The indicating panel of paragraph A0, wherein the second indicator is a colorimetric indicator A5. The indicating panel of paragraph A0, wherein at least one of the first indicator and second indicator is a pH indicator.

A6. The indicating panel of paragraph A0, wherein at least one of the first indicator and second indicator is a metal ion indicator.

A7. The indicating panel of paragraph A0, wherein the first indicator is PMVEMA.

A8. The indicating panel of paragraph A7, wherein the second indicator is a pH indicator.

A9. The indicating panel of paragraph A0, wherein the polymeric mordant is a polymeric cationic surfactant.

A10. The indicating panel of paragraph A0, wherein the polymeric mordant is poly[methyl acrylate-co-(3-acrylamidopropyl)trimethyl ammonium chloride].

B0. An indicating incontinence product, comprising:
an absorbent core;
a porous inner sheet adjacent to the absorbent core that is impregnated with a first indicator;
    wherein the first indicator is selected to respond to a target analyte by creating a detectable response; and
a porous outer sheet adjacent to the inner sheet, wherein the outer sheet is impregnated with a polymeric mordant selected to stabilize indicators that generate detectable responses.

B1. The incontinence product of paragraph B0, wherein the absorbent core includes a superabsorbent polymer.

B2. The incontinence product of paragraph B0, wherein the absorbent core includes a superabsorbent sodium polyacrylate polymer.

C0. An indicating incontinence product, comprising:
an absorbent core;
a porous inner sheet adjacent to the absorbent core; wherein the inner sheet is impregnated with a pair of coupled indicators;
    wherein the first indicator of the coupled pair is selected to respond to a target analyte by creating a reporting condition; and
    wherein the second indicator is selected to respond to the reporting condition by generating a detectable response;
a porous outer sheet adjacent to the inner sheet, wherein the outer sheet is impregnated with a polymeric mordant selected to irreversibly stabilize the second indicator that is generating the detectable response.

C1. The indicating incontinence product of paragraph C0, further comprising a reference panel disposed adjacent to the absorbent core, where the reference panel includes a substantially white and porous material.

C2. The indicating incontinence product of paragraph C1, wherein the reference panel is configured so that, upon absorption of a urine sample, a color of the reference panel will substantially correspond to that of the urine sample.

D0. An indicating panel for an incontinence product, comprising:
a porous sheet that is impregnated with
a first indicator that is selected to respond to a target analyte by creating a detectable response; and
a polymeric mordant that is selected to stabilize indicators that generate detectable responses, wherein the polymeric mordant has been stabilized with respect to both basic and thermal degradation.

D1. The indicating panel of paragraph D0, wherein the polymeric mordant has been stabilized with respect to cross-reactivity with the first indicator.

D2. The indicating panel of paragraph D0, wherein the porous inner sheet further includes a second indicator, wherein the second indicator is selected to respond to the detectable response of the first indicator by generating a second detectable response.

D3. The indicating panel of paragraph D0, wherein the first indicator is a colorimetric indicator.

D4. The indicating panel of paragraph D2, wherein the second indicator is a colorimetric indicator D5. The indicating panel of paragraph D2, wherein at least one of the first indicator and second indicator is a pH indicator.

D6. The indicating panel of paragraph D2, wherein at least one of the first indicator and second indicator is a metal ion indicator.

D7. The indicating panel of paragraph D0, wherein the first indicator is PMVEMA.

D8. The indicating panel of paragraph D7, wherein the second indicator is a pH indicator.

D9. The indicating panel of paragraph D0, wherein the polymeric mordant is derivatized by a plurality of quaternary ammonium functional groups; and wherein each proton beta to each quaternary ammonium functional group is replaced by a lower alkyl having 1-6 carbons.

E0. An indicating incontinence product, comprising:
an absorbent core;
a porous inner sheet adjacent to the absorbent core that is impregnated with a first indicator, a second indicator, and a polymeric mordant; wherein
the first indicator is selected to respond to a target analyte by creating a detectable response;

the second indicator is selected to respond to the detectable response of the first indicator by generating a second detectable response; and the polymeric mordant is selected to stabilize indicators that generate detectable responses, and has been stabilized with respect to basic degradation, thermal degradation, and cross-reactivity with the first indicator.

E1. The incontinence product of paragraph E0, wherein the absorbent core includes a superabsorbent polymer.

E2. The incontinence product of paragraph E0, wherein the absorbent core includes a superabsorbent sodium polyacrylate polymer.

E3. The incontinence product of paragraph E0, wherein the polymeric mordant is selected to irreversibly stabilize the second indicator that is generating the detectable response.

F0. A calcium ion indicating panel for an incontinence product, comprising:

a porous inner sheet that is impregnated with either cresolphthalein-complexone or thymolphthalein-complexone, a basic buffering agent, and a $Mg^{+2}$ inhibitor; and a porous outer sheet adjacent to the inner sheet, wherein the outer sheet is impregnated with poly[methyl acrylate-co-(3-acrylamidopropyl)trimethyl ammonium chloride].

F1. The calcium ion indicating panel of paragraph F0, further comprising a separation layer disposed between the inner sheet and the outer sheet, wherein the separation layer is at least one of water-soluble and porous.

F2. The calcium ion indicating panel of paragraph F0, wherein the cresolphthalein-complexone or thymolphthalein-complexone is present in the inner sheet at a concentration of 0.5-1 wt %; the basic buffering agent is present in the inner sheet at a concentration of 1-2 wt %; and the $Mg^{2+}$ inhibitor is present in the inner sheet at a concentration of 1-2 wt %.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. An indicating panel for an incontinence product, comprising:
   a porous inner sheet that is impregnated with a first indicator;
   wherein the first indicator is selected to respond to a target analyte by creating a detectable response;
   a porous outer sheet adjacent to the inner sheet, wherein the outer sheet is impregnated with a polymeric mordant selected to stabilize indicators that generate detectable responses; and
   a separation layer disposed between the inner sheet and the outer sheet, wherein the separation layer is at least water-soluble.

2. The indicating panel of claim 1, wherein the porous inner sheet further includes a second indicator, wherein the second indicator is selected to respond to the detectable response of the first indicator by generating a second detectable response.

3. The indicating panel of claim 1, wherein the first indicator is a colorimetric indicator.

4. The indicating panel of claim 2, wherein the second indicator is a colorimetric indicator.

5. The indicating panel of claim 2, wherein at least one of the first indicator and second indicator is a pH indicator.

6. The indicating panel of claim 2, wherein at least one of the first indicator and second indicator is a metal ion indicator.

7. The indicating panel of claim 1, wherein the first indicator is poly(methyl vinyl ether-alt-maleic acid) (PM-VEMA).

8. The indicating panel of claim 2, wherein the second indicator is a pH indicator.

9. The indicating panel of claim 1, wherein the separation layer is porous.

10. The indicating panel of claim 1, wherein the polymeric mordant is a polymeric cationic surfactant.

11. The indicating panel of claim 1, wherein the polymeric mordant is poly[methyl acrylate-co-(3-acrylamidopropyl) trimethyl ammonium chloride].

12. An indicating incontinence product, comprising:
    an absorbent core;
    a porous inner sheet adjacent to the absorbent core that is impregnated with a first indicator;
    wherein the first indicator is selected to respond to a target analyte by creating a detectable response;
    a porous outer sheet adjacent to the inner sheet, wherein the outer sheet is impregnated with a polymeric mordant selected to stabilize indicators that generate detectable responses; and
    a separation layer disposed between the inner sheet and the outer sheet, wherein the separation layer is at least one of water-soluble and porous.

13. The incontinence product of claim 12, wherein the absorbent core includes a superabsorbent polymer.

14. The incontinence product of claim 12, wherein the absorbent core includes a superabsorbent sodium polyacrylate polymer.

15. An indicating system for an incontinence product, comprising:
    an indicating panel including:
    a porous inner sheet impregnated with a pair of coupled indicators,
    wherein a first indicator of the coupled pair is selected to respond to a target analyte by creating a reporting condition, wherein a second indicator of the coupled pair is selected configured to respond to the reporting condition by generating a detectable response,
a porous outer sheet adjacent to the inner sheet, wherein the outer sheet is impregnated with a polymeric mordant selected to irreversibly stabilize the second indicator that is generating the detectable response, and
a separation layer disposed between the inner sheet and the outer sheet, wherein the separation layer is at least one of water-soluble and porous; and
a reference panel disposed adjacent to the indicating panel, where the reference panel includes a substantially white and porous material.

16. The indicating system of claim 15, wherein the reference panel includes a cellulose-based filter paper.

17. The indicating system of claim 15, wherein the first and second indicators are selected to produce a detectable response that is a distinct color change in the presence of the target analyte.

18. The indicating system of claim 15, wherein the reference panel is configured so that, upon absorption of a urine sample, a color of the reference panel will substantially correspond to that of the urine sample.

19. The indicating system of claim 18, wherein color data of the indicating panel is configured to be scanned by an optical device coupled to a processor, and the processor is capable of processing the color data so as to detect and/or quantify a presence of the target analyte.

20. The indicating system of claim 19, wherein the processor is additionally capable of using a color of the reference panel to control for urine color when processing the color data.

21. An indicating panel for an incontinence product, comprising:
a porous inner sheet that is impregnated with a first indicator;
wherein the first indicator is selected to respond to a target analyte by creating a detectable response;
a porous outer sheet adjacent to the inner sheet, wherein the outer sheet is impregnated with a polymeric mordant selected to stabilize indicators that generate detectable responses; and
a separation layer disposed between the inner sheet and the outer sheet, wherein the separation layer is at least porous.

22. The indicating panel of claim 21, wherein the porous inner sheet further includes a second indicator, wherein the second indicator is selected to respond to the detectable response of the first indicator by generating a second detectable response.

23. The indicating panel of claim 21, wherein the first indicator is a colorimetric indicator.

24. The indicating panel of claim 22, wherein the second indicator is a colorimetric indicator.

25. The indicating panel of claim 22, wherein at least one of the first indicator and second indicator is a pH indicator.

26. The indicating panel of claim 22, wherein at least one of the first indicator and second indicator is a metal ion indicator.

27. The indicating panel of claim 22, wherein the second indicator is a pH indicator.

28. The indicating panel of claim 21, wherein the polymeric mordant is a polymeric cationic surfactant.

29. An indicating panel for an incontinence product, comprising:
a porous inner sheet that is impregnated with a first indicator;
wherein the first indicator is selected to respond to a target analyte by creating a detectable response; and
a porous outer sheet adjacent to the inner sheet, wherein the outer sheet is impregnated with a polymeric mordant selected to stabilize indicators that generate detectable responses;
wherein the polymeric mordant is poly[methyl acrylate-co-(3-acrylamidopropyl)trimethyl ammonium chloride].

30. An indicating panel for an incontinence product, comprising:
a porous inner sheet that is impregnated with a first indicator;
wherein the first indicator comprises poly(methyl vinyl ether-alt-maleic acid) (PMVEMA) and is configured to respond to a target analyte by creating a detectable response; and
a porous outer sheet adjacent to the inner sheet, wherein the outer sheet is impregnated with a polymeric mordant selected to stabilize indicators that generate detectable responses.

* * * * *